(12) United States Patent
Arendt (10) Patent No.: US 8,413,811 B1
(45) Date of Patent: Apr. 9, 2013

(54) DISPENSER PACKAGE FOR MEDICAL/DENTAL DEVICES

(76) Inventor: Thomas Arendt, Norwalk, WI (US)

( * ) Notice: Subject to any disclaimer, the term of this patent is extended or adjusted under 35 U.S.C. 154(b) by 152 days.

(21) Appl. No.: 12/928,785

(22) Filed: Dec. 20, 2010

(51) Int. Cl.
 B65D 83/10 (2006.01)
(52) U.S. Cl. .................... 206/368; 206/365; 206/63.5
(58) Field of Classification Search .................. 206/364, 206/365, 366, 368, 63.5; 604/192, 198, 403; 220/4.22, 4.23, 4.24
See application file for complete search history.

(56) References Cited

U.S. PATENT DOCUMENTS

| 3,127,985 | A |  | 4/1964 | Scott |  |
|---|---|---|---|---|---|
| 4,512,474 | A |  | 4/1985 | Harding |  |
| 4,671,408 | A | * | 6/1987 | Raines et al. | 206/365 |
| 4,921,096 | A | * | 5/1990 | McFarlane | 206/349 |
| 5,090,564 | A | * | 2/1992 | Chimienti | 206/365 |
| 5,090,570 | A |  | 2/1992 | Todd |  |
| 5,125,521 | A | * | 6/1992 | Somogyi | 215/12.1 |
| 5,368,160 | A |  | 11/1994 | Leuschen et al. |  |
| 5,405,005 | A |  | 4/1995 | White |  |
| 5,474,179 | A |  | 12/1995 | Iosif et al. |  |
| 5,538,428 | A |  | 7/1996 | Staubli |  |
| 5,842,567 | A |  | 12/1998 | Rowe et al. |  |
| 5,961,330 | A |  | 10/1999 | Hanson |  |
| 6,012,580 | A |  | 1/2000 | Peters et al. |  |
| 6,561,805 | B2 |  | 5/2003 | Kumar |  |
| 6,889,839 | B1 |  | 5/2005 | Rosten et al. |  |
| 6,913,465 | B2 |  | 7/2005 | Howlett et al. |  |
| 7,114,624 | B2 | * | 10/2006 | Van Parys | 215/12.1 |
| 7,770,722 | B2 |  | 8/2010 | Donahoe et al. |  |
| 2001/0037954 | A1 | * | 11/2001 | Schmidt et al. | 206/364 |
| 2004/0112781 | A1 |  | 6/2004 | Hofverberg et al. |  |
| 2004/0211689 | A1 | * | 10/2004 | Torris et al. | 206/364 |

\* cited by examiner

Primary Examiner — David Fidei
(74) Attorney, Agent, or Firm — Tipton L. Randall (57) ABSTRACT

A dispenser container assembly for storing and dispensing a medical/dental device comprises a support section, including first and second opposed clamshell halves pivoted together at a flexible hinge. Each clamshell half has a contact edge mating with a like contact edge of an opposed half to form a contained space therein. Each contact edge also has a feature mating with a like feature of an opposed contact edge to produce a mounting aperture for supporting a medical/dental device within the contained space. A cap section has a closed end and an open end that engages the support section to maintain the first and second opposed clamshell halves in a closed condition and to enclose an exterior portion of the medical/dental device supported in the mounting aperture of the support section.

13 Claims, 6 Drawing Sheets

DISPENSER PACKAGE FOR MEDICAL/DENTAL DEVICES

CROSS-REFERENCE TO RELATED APPLICATIONS, IF ANY

Not applicable.

STATEMENT REGARDING FEDERALLY SPONSORED RESEARCH OR DEVELOPMENT

Not applicable.

REFERENCE TO A MICROFICHE APPENDIX, IF ANY

Not applicable.

BACKGROUND OF THE INVENTION

1. Field of the Invention

The present invention relates to packaging and, more particularly, to packaging for medical/dental devices and, most particularly, to a dispenser package for medical/dental devices.

2. Background Information

Numerous medical and dental devices are provided to the user in a package that prevents contamination of the device. The packaging not only prevents damage to the device during shipment, but the device and packaging can be sterilized to prevent microbial contamination of these devices. This is particularly important for various implants that are inserted into a patient's body. Devices such as hip, knee and shoulder joints, as well as dental implants must be sterile when implanted into a patient. A number of such packages have received patents. These include patents by Leuschen et al., U.S. Pat. No. 5,368,160; Staubli, U.S. Pat. No. 5,538,428; Hanson, U.S. Pat. No. 5,961,330; Peters et al., U.S. Pat. No. 6,012,580; Kumar, U.S. Pat. No. 6,561,805; Howlett et al., U.S. Pat. No. 6,913,465; Donahoe et al., U.S. Pat. No. 7,770,722 and Hofverberg et al., U.S. Pub. No. 2004/0112781; all of which disclose packaging used for dental implants. Packaging that employs a "clam shell" type design for other objects includes U.S. Pat. No. 3,127,985 by Scott; U.S. Pat. No. 4,512,474 by Harding; U.S. Pat. No. 5,090,570 by Todd; U.S. Pat. No. 5,474,179 by Iosif et al.; and U.S. Pat. No. 5,842,567 by Rowe et al.

Applicant has devised a sterilizable, dispenser container assembly for storing and dispensing a medical/dental device that provides a unique improvement over existing packaging.

SUMMARY OF THE INVENTION

The invention is directed to a dispenser container assembly for storing and dispensing a medical/dental device. The container assembly comprises a support section, including first and second opposed clamshell halves, pivoted together at a flexible hinge. Each clamshell half has a contact edge mating with a like contact edge of an opposed half to form a contained space therein. Each contact edge also has a feature mating with a like feature of an opposed contact edge to produce a mounting aperture for supporting a medical/dental device within the contained space. A cap section has an open end and a closed end. The open end engages the support section to maintain the first and second opposed clamshell halves in a closed condition and to enclose an exterior portion of the medical/dental device supported in the mounting aperture of the support section.

Current FDA regulations for sterile packaging of medical/dental devices require enclosures having two separate seals, both of which maintain enclosure sterility for three (3) years. To meet these requirements, the dispenser container assembly of the present invention, with a contained medical/dental device therein, is enclosed first in one, and then in a second sealed, medical grade blister pack for sterilization and storage. A user can remove the blister packs and grasp the dispenser container assembly to access the sterile medical/dental device. Then, with a suitable tool, the user places the sterile device into the prepared site, without touching or contaminating the medical/dental device.

In a preferred embodiment of the invention, the dispenser container assembly for storing and dispensing a medical/dental device comprises a support section including first and second opposed clamshell halves pivoted together at a flexible hinge. Each clamshell half has a contact edge mating with a like contact edge of an opposed half to form a contained space therein. Each contact edge also has a feature mating with a like feature of an opposed contact edge to produce a mounting aperture for supporting a medical/dental device within the contained space. The support section in a closed condition includes a cylindrical exterior surface adjacent the mounting aperture. A cap section has an open end and a closed end. The cap section has an interior cylindrical surface at the open end for engaging the cylindrical exterior surface of the support section to maintain the first and second opposed clamshell halves in a closed condition and to enclose an exterior portion of the medical/dental device supported in the mounting aperture of the support section. A locking mechanism is present for securing the cap section to the support section.

DESCRIPTION OF THE EMBODIMENTS

| Nomenclature | |
|---|---|
| 10 | Dispenser Container Assembly |
| 20 | Support Section of Container Assembly |
| 22 | First Clam Shell Half |
| 24 | Second Clam Shell Half |
| 26 | Contact Edge of Shell Halves |
| 28 | Mating Feature of Contact Edge |
| 30 | Flexible Hinge |

-continued

| | Nomenclature |
|---|---|
| 32 | Contained Space of Support Section |
| 34 | Mounting Aperture of Support Section |
| 40 | Cap Section of Container Assembly |
| 42 | Open End of Cap Section |
| 44 | Closed End of Cap Section |
| 46 | Interior Contact Surface of Closed End of Cap Section |
| 50 | Opposed Exterior Flat Surfaces of Support Section |
| 60 | Opposed Exterior Flat Surfaces of Cap Section |
| 70 | Cylindrical Exterior Surface of Support Section |
| 75 | Cylindrical Interior Surface of Cap Section |
| 80 | Locking Mechanism |
| 85 | Ridges of Locking Mechanism |
| 90 | Grooves of Locking Mechanism |
| D | Medical/Dental Device |
| E | Exterior Portion of Medical/Dental Device |

Construction

The invention is a dispenser container assembly for storing and dispensing a medical/dental device. The container assembly comprises a support section, including first and second opposed clamshell halves, pivoted together at a flexible hinge. Each clamshell half has a contact edge mating with a like contact edge of an opposed half to form a contained space therein. Each contact edge also has a feature mating with a like feature of an opposed contact edge to produce a mounting aperture for supporting a medical/dental device within the contained space. The support section in a closed condition includes a cylindrical exterior surface adjacent the mounting aperture.

A cap section has an open end and a closed end. The cap section has an interior cylindrical surface at the open end for engaging the cylindrical exterior surface of the support section to maintain the first and second opposed clamshell halves in a closed condition and to enclose an exterior portion of the medical/dental device supported in the mounting aperture of the support section. A locking mechanism is present for securing the cap section to the support section.

Figure 1:
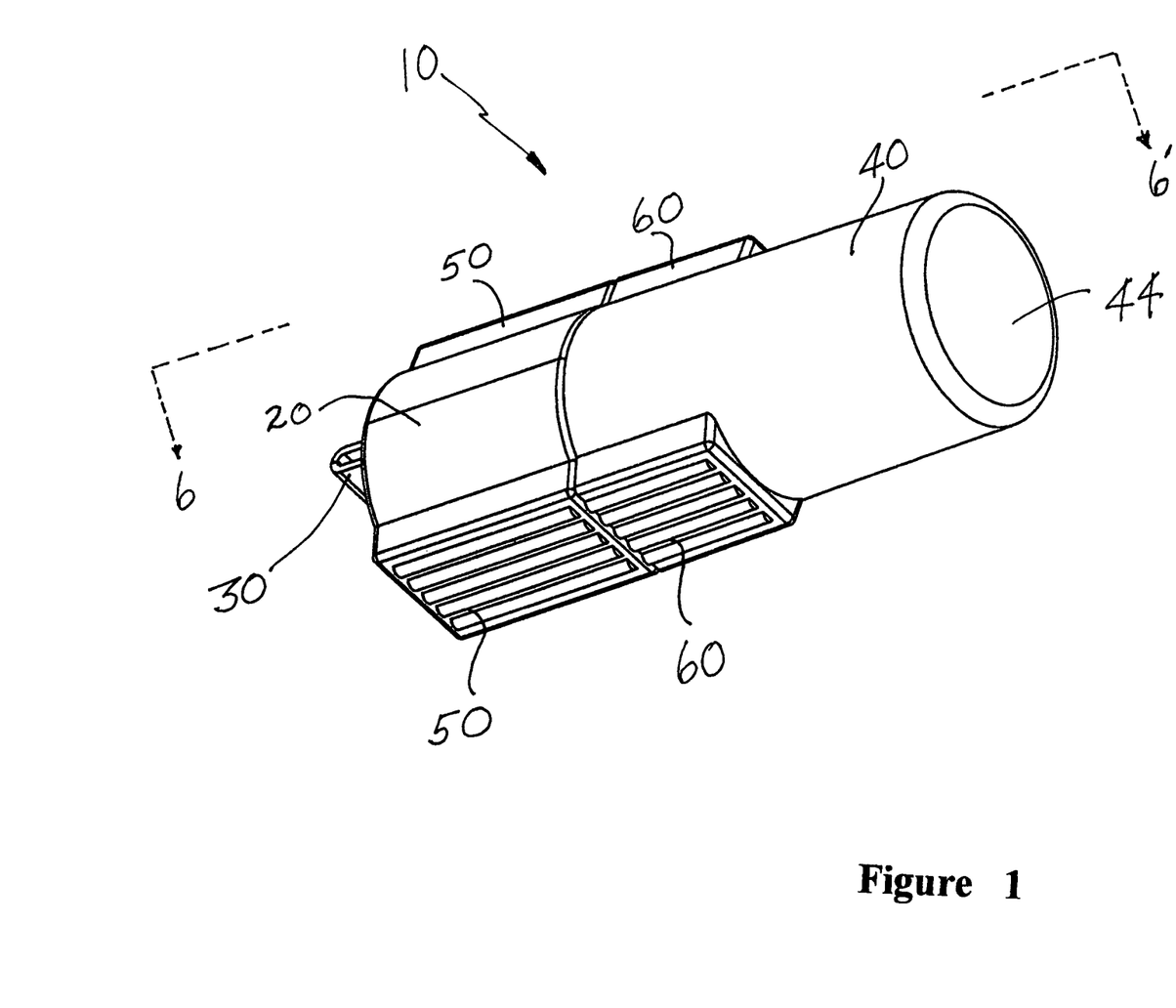
FIG. 1 is a perspective view of the closed, dispenser container assembly of the present invention.
Figure 2:
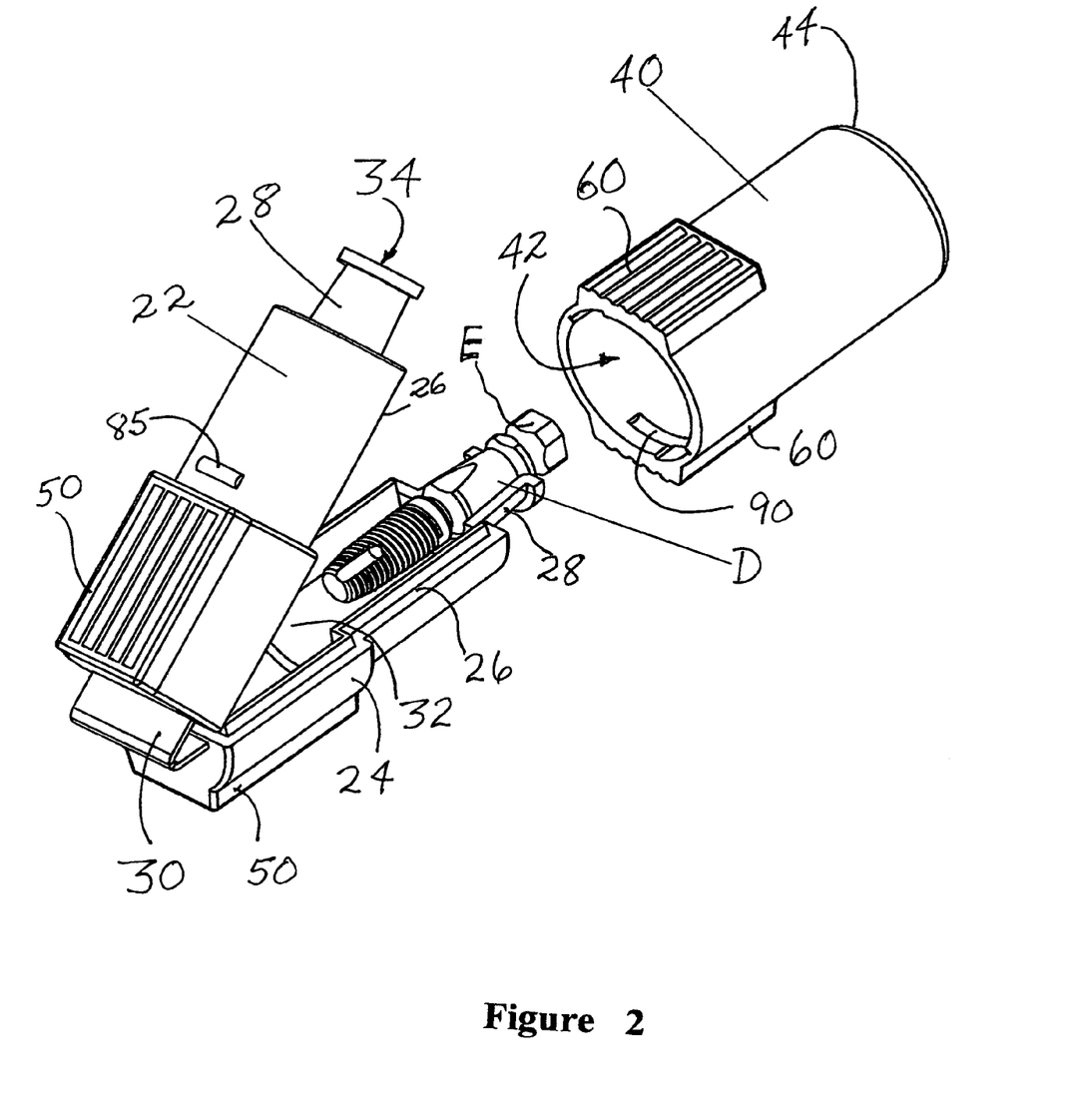
FIG. 2 is a perspective view of the opened, dispenser container assembly of the present invention containing a medical/dental device.

Referring now to FIGS. 1 and 2, the dispenser container assembly 10 for storing and dispensing a medical/dental device D is shown in a closed and a partially opened condition, respectively. The container assembly 10 comprises a support section 20, including a first clamshell half 22 and a second clamshell half 24, the opposed clamshell halves 22, 24 pivoted together at a flexible hinge 30. Preferably, the flexible hinge 30 biases apart the clamshell halves 22, 24 of the support section 20, as illustrated in FIG. 2. Each clamshell half 22, 24 has a contact edge 26 mating with a like contact edge 26 of an opposed clamshell half 22, 24 to form a contained space 32 therein, with the contact edges 26 of the opposed clamshell halves 22, 24 brought together. Each contact edge 26 also has a feature 28 mating with a like feature 28 of an opposed contact edge 26 to produce a mounting aperture 34 for supporting a medical/dental device D within the contained space 32, again with the contact edges 26 of the opposed clamshell halves 22, 24 brought together. Preferably, the mounting aperture 34, formed by the mating features 28 of the opposed contact edges 26 of the clamshell halves 22, 24, is positioned opposite the flexible hinge 30.

The support section 20 in a closed condition includes a cylindrical exterior surface 70 adjacent the mounting aperture 34. In the present embodiment, the medical/dental device D is a dental implant that is secured in the mounting aperture 34 and supported within the contained space 32 of the support section 20. Other medical/dental devices D of larger size can be accommodated in a dispenser container assembly 10 of an appropriately large size with equivalent results.

Figure 3:
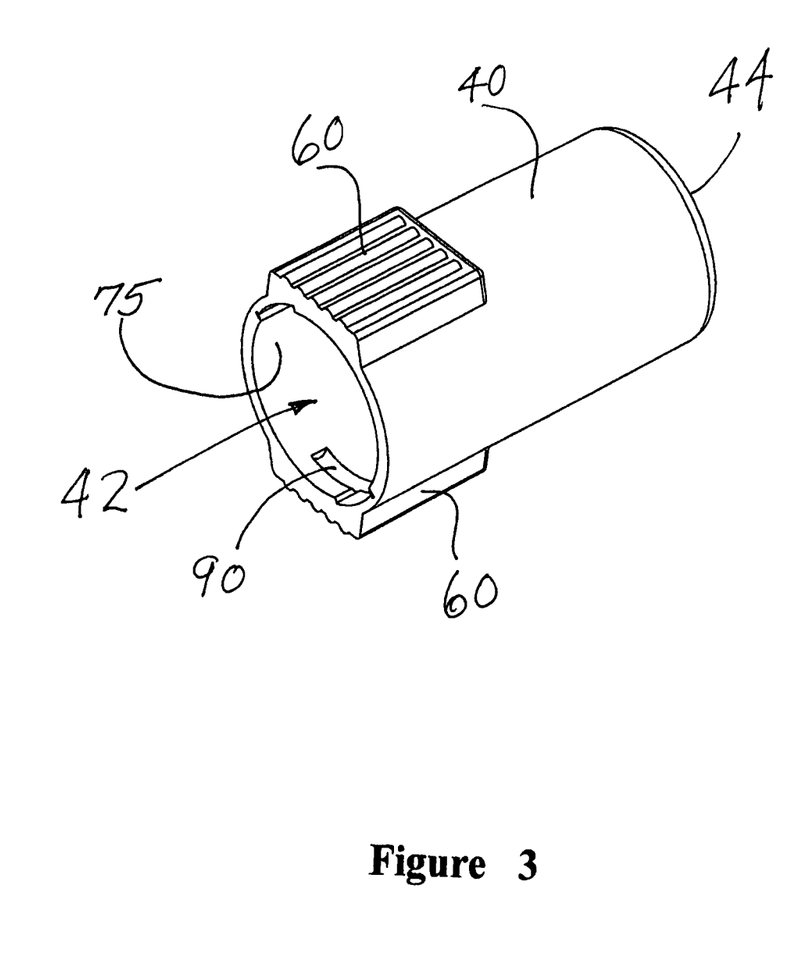
FIG. 3 is a perspective view of the cap section of the dispenser container assembly of the present invention.
Figure 4:
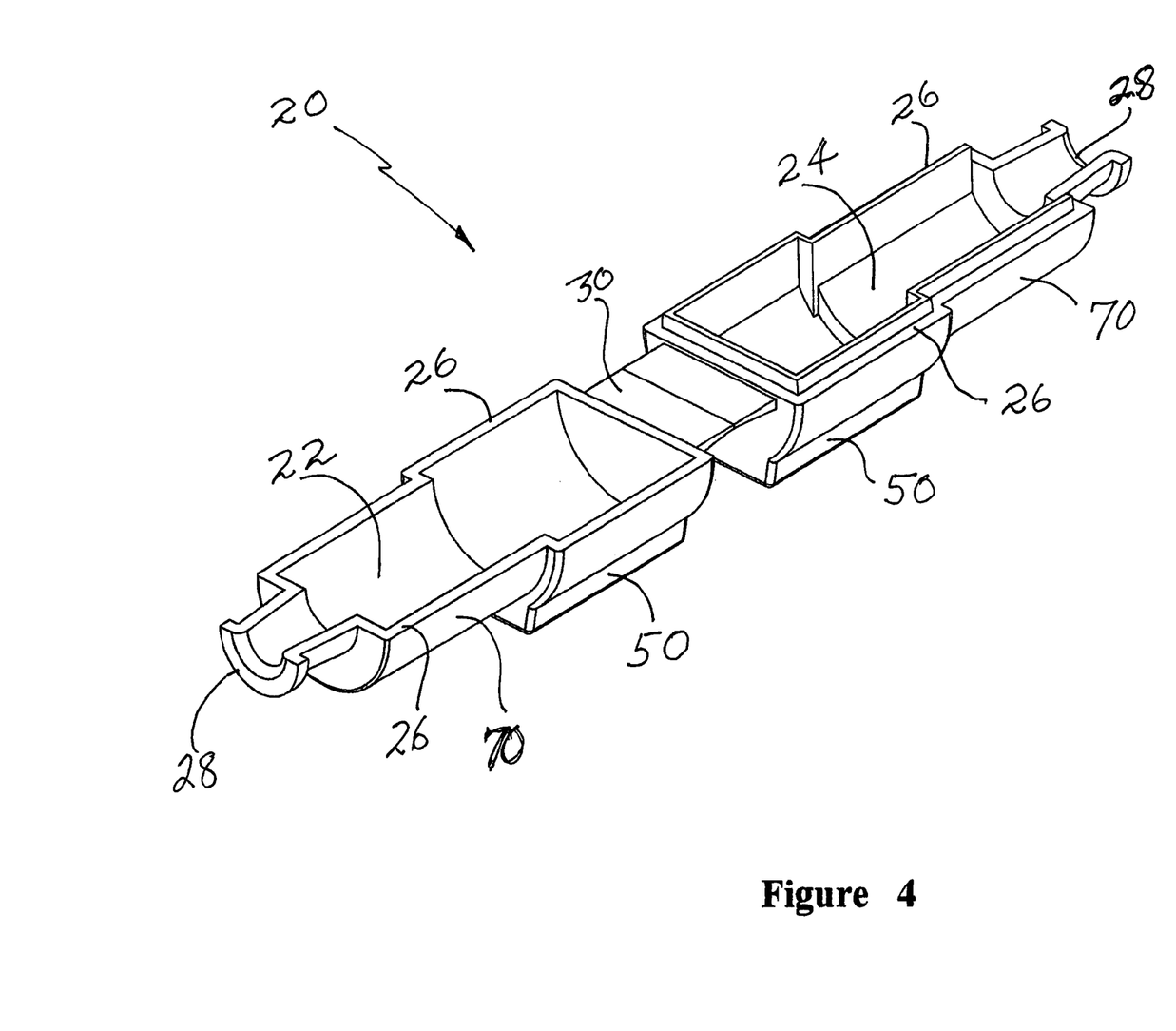
FIG. 4 is a perspective view of the fully opened, support section of the dispenser container assembly of the present invention.

As shown in FIG. 3, a cap section 40 of the container assembly 10 has an open end 42 and a closed end 44. The cap section 40 has an interior cylindrical surface 75, at least at the open end 42 thereof, for engaging the cylindrical exterior surface 70 of the support section 20 to maintain the first and second opposed clamshell halves 22, 24 in a closed condition. The cap section also encloses an exterior portion E of the medical/dental device D, supported in the mounting aperture 34 of the support section 20 when secured to the closed support section 20. In addition, the closed end 44 of the cap section 40 includes an interior contact surface 46 that abuts the portion of the support section 20 adjacent the mounting aperture 34 thereof, with the cap section 40 engaged with the support section 20. The interior contact surface 46 is best seen in the cross sectional view of FIG. 6.

Figure 5:
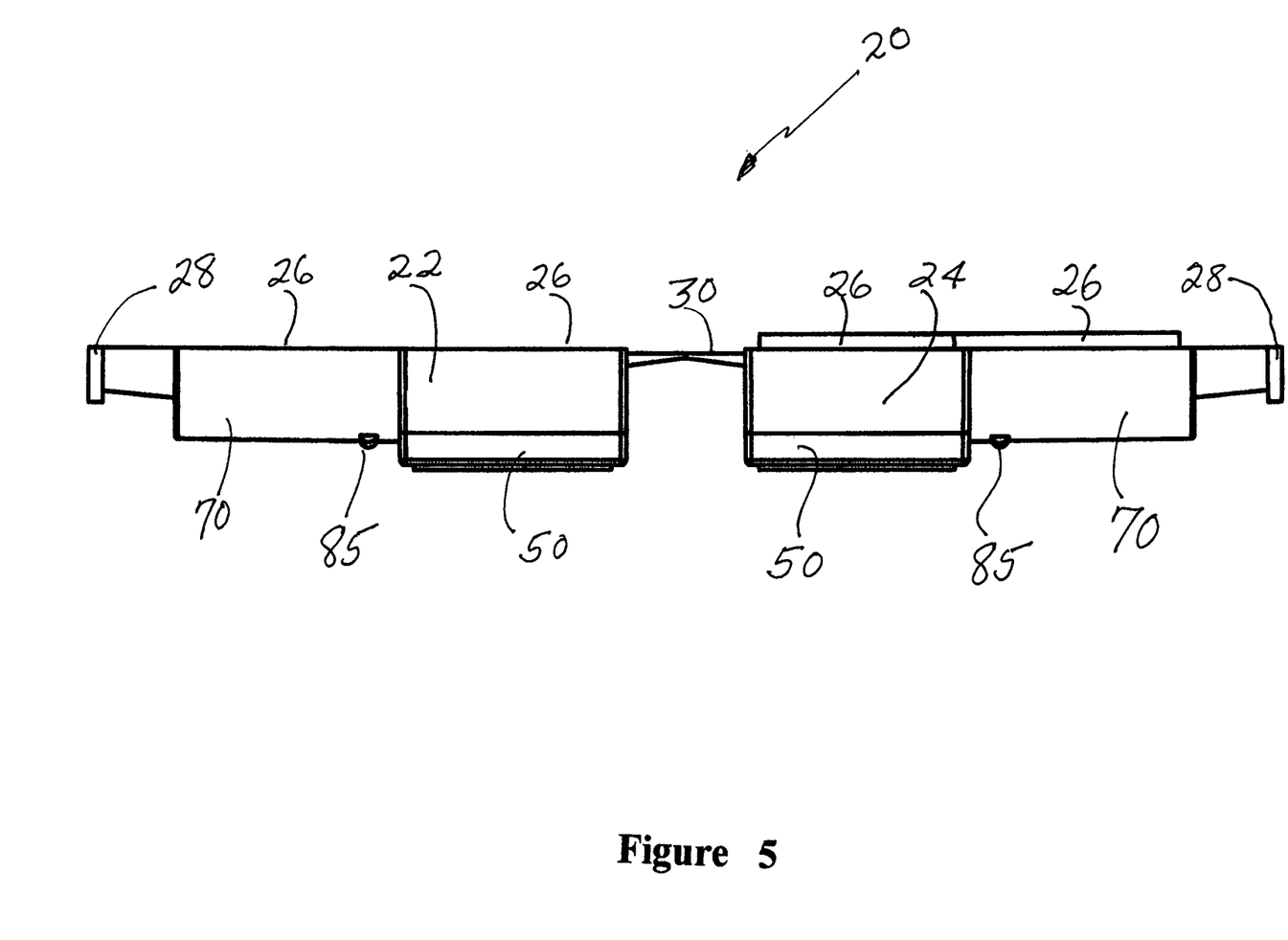
FIG. 5 is a perspective side view of the fully opened, support section of the dispenser container assembly of the present invention.
Figure 6:
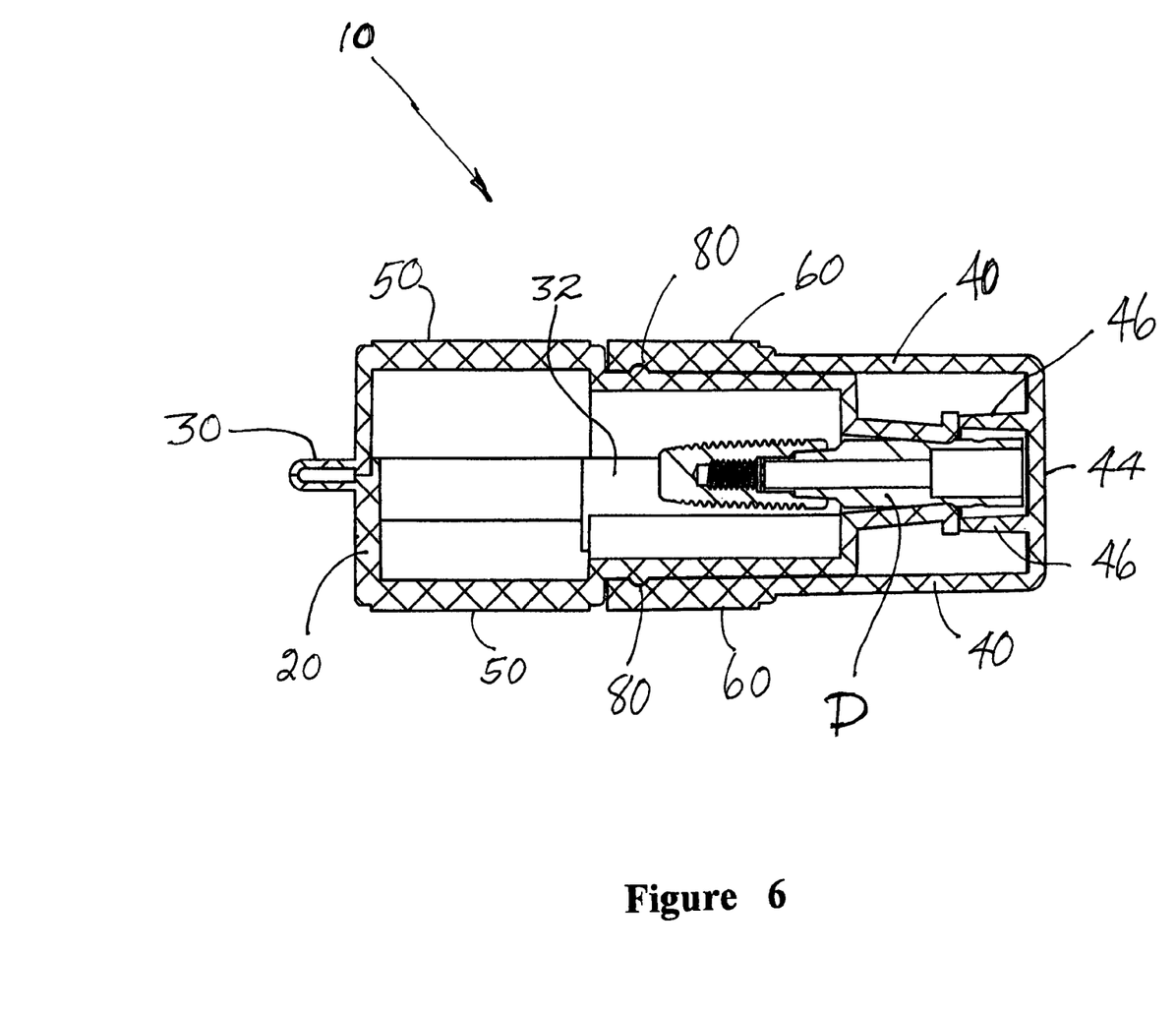
FIG. 6 is a cross sectional view along line 6-6' of FIG. 1 of the dispenser container assembly of the present invention.

A locking mechanism 80 is present for securing the cap section 40 to the support section 20 in the closed condition. In the present embodiment, the locking mechanism 80 includes one or more ridges' 85 on the cylindrical exterior surface 70 of the support section 20, as seen in FIGS. 5 and 6, and a corresponding number of grooves 90 on the interior cylindrical surface 75 of the cap section 40, as seen in FIGS. 3 and 6. Alternatively, the location of the ridges 85 and grooves 90 on the two cylindrical surfaces 70, 90 can be reversed with equivalent results. To lock the cap section 40 to the support section 20, the cylindrical surface 70 of the support section 20 is inserted into the open end 42 of the cap section 40 with the ridges 85 and grooves 90 unaligned. Rotating one section relative to the other section brings the ridges 85 into the grooves 90 and prevents removal of the cap section 40 from the support section 20, as illustrated in FIG. 1. Unlocking the two joined sections 20, 40 is achieved by rotating one section relative to the other section, but opposite the relative rotation employed to lock the two sections 20, 40. Other locking mechanisms 80 are contemplated that produce equivalent results.

In a further embodiment of the invention, the support section 20 includes a pair of opposed, exterior flat surfaces 50, and the cap section 40 includes a pair of opposed, exterior flat surfaces 60. The pairs of opposed, flat surfaces 50, 60 enable grasping of each section 20, 40 by an individual to lock and unlock the container assembly 10, as well as providing ease of handling during removal of the medical/dental device D from the support section 20 of the container assembly 10. The presence of the pairs of opposed, exterior flat surfaces 50, 60 is particularly useful for the container assembly 10 sized to contain a dental implant D. An individual easily grasps the flat surfaces 50, 60 of each section 20, 40 between the thumb and forefinger to open or close the container assembly 10. As illustrated in FIG. 2, the dental implant remains supported in the mating feature 28 of one of the clam shell halves 24, even with the support section 20 in an open condition.

Preferably, the dispenser container assembly 10 for storing and dispensing a medical/dental device D, including the support section 20 and the cap section 40, is fabricated from a sterilizable polymeric resin material. Fabrication is conveniently achieved by injection molding of each section using polymeric resin material. Consequently, the dispenser container assembly 10 containing the medical/dental device D can be further packaged, then sterilized and maintained in a sterile condition until the medical/dental device D is needed.

Current FDA regulations require that medical/dental implant products are maintained sterile for its entire shelf life of three years. Whether the package is a vial, a blister pack or a peelable pouch, there must be not one, but two seals that are each tested and validated to maintain sterility for 3 years. In the present invention, the dispenser container assembly 10 is fitted within a sealed medical grade blister pack, and that entire unit is sealed within another medical grade blister pack. The main function of the dispenser container assembly 10 is to allow the dentist to remove the blister packages and attach a wrench or thumb wheel to the exterior portion E of the implant carrier, without ever touching the implant D itself. After a wrench or thumbwheel is attached, the remaining support section 20 of the dispenser container assembly 10 easily falls away, and the implant D is placed into the prepared site.

In the case of bone screws, most such medical devices are currently packed in blister trays, which contain numerous parts that are typically required for trauma situations. Such packaging requires that the bone screws, etc. must be handled by a surgeon or assistant to attach drivers or other tools for placement. It is contemplated that the dispenser container assembly 10 of the present invention, with suitable sterilizable packaging, can function to allow surgeons to attach drivers without touching the actual bone screw.

While the invention has been particularly shown and described with reference to preferred embodiments thereof, it will be understood by those skilled in the art that various changes in form and details may be made therein without departing from the spirit and scope of the invention.

I claim:

1. A dispenser container assembly for storing and dispensing a dental implant device, the container assembly comprising:
    a support section including first and second opposed clamshell halves pivoted together at a flexible hinge, each half having a contact edge mating with a like contact edge of an opposed half to form a contained space therein, each contact edge having a feature mating with a like feature of an opposed contact edge to produce a mounting aperture for supporting a dental implant device within the contained space, the support section in a closed condition including a cylindrical exterior surface adjacent the mounting aperture;
    a cap section having an open end and a closed end, the open end engaging the support section to maintain the first and second opposed clamshell halves in a closed condition and to enclose an exterior portion of the dental implant device supported in the mounting aperture of the support section, the cap section including cylindrical interior and exterior surfaces at the open end thereof; and
    a pair of opposed, exterior flat surfaces on the exterior surface of the cylindrical support section in a closed condition and a pair of opposed, exterior flat surfaces on the cylindrical exterior surface of the cap section, the pairs of opposed, exterior flat surfaces adapted for grasping by an individual.

2. The dispenser container assembly for storing and dispensing a dental implant device of claim 1, further including a locking mechanism for securing the cap section to the support section.

3. The dispenser container assembly for storing and dispensing a dental implant device of claim 1, wherein the flexible hinge biases apart the clamshell halves of the support section.

4. The dispenser container assembly for storing and dispensing a dental implant device of claim 1, wherein the aperture formed by the features of the opposed contact edges of the clamshell halves is positioned opposite the flexible hinge.

5. The dispenser container assembly for storing and dispensing a dental implant device of claim 1, wherein the support section and the cap section are fabricated from a sterilizable polymeric resin material.

6. A dispenser container assembly for storing and dispensing a dental implant device, the container assembly comprising:
    a support section including first and second opposed clamshell halves pivoted together at a flexible hinge, each half having a contact edge mating with a like contact edge of an opposed half to form a contained space therein, each contact edge having a feature mating with a like feature of an opposed contact edge to produce a mounting aperture for supporting a dental implant device within the contained space, the support section in a closed condition including a cylindrical exterior surface adjacent the mounting aperture;
    a cap section having an open end and a closed end, the open end engaging the support section to maintain the first and second opposed clamshell halves in a closed condition and to enclose an exterior portion of the dental implant device supported in the mounting aperture of the support section, the cap section including cylindrical interior and exterior surfaces at the open end thereof; and
    a pair of opposed, exterior flat surfaces on the exterior surface of the cylindrical support section in a closed condition and a pair of opposed, exterior flat surfaces on the cylindrical exterior surface of the cap section, the pairs of opposed, exterior flat surfaces adapted for grasping by an individual; and
    a locking mechanism for securing the cap section to the support section.

7. The dispenser container assembly for storing and dispensing a dental implant device of claim 6, wherein the flexible hinge biases apart the clamshell halves of the support section.

8. The dispenser container assembly for storing and dispensing a medical/dental dental implant device of claim 6, wherein the aperture formed by the features of the opposed contact edges of the clamshell halves is positioned opposite the flexible hinge.

9. The dispenser container assembly for storing and dispensing a dental implant device of claim 6, wherein the support section and the cap section are fabricated from a sterilizable polymeric resin material.

10. A dispenser container assembly for storing and dispensing a dental implant device, the container assembly comprising:
    a support section including first and second opposed clamshell halves pivoted together at a flexible hinge, each half having a contact edge mating with a like contact edge of an opposed half to form a contained space therein, each contact edge having a feature mating with a like feature of an opposed contact edge to produce a mounting aperture for supporting a dental implant device within the contained space, the support section in a closed condition including a cylindrical exterior surface adjacent the mounting aperture;
    a cap section having an open end and a closed end, the cap section having an interior and exterior cylindrical surfaces at the open end for engaging the cylindrical exterior surface of the support section to maintain the first and second opposed clamshell halves in a closed condition and to enclose an exterior portion of the dental implant device supported in the mounting aperture of the support section;
    a pair of opposed, exterior flat surfaces on the exterior surface of the cylindrical support section in a closed condition and a pair of opposed, exterior flat surfaces on the cylindrical exterior surface of the cap section, the pairs of opposed, exterior flat surfaces adapted for grasping by an individual; and a locking mechanism for securing the cap section to the support section, the locking mechanism including at least one ridge on the cylindrical, exterior surface of the support section and at least one groove on the cylindrical, interior surface of the cap section, the at least one ridge engaging the at least one groove by rotational movement between the support section and the cap section.

11. The dispenser container assembly for storing and dispensing a dental implant device of claim 10, wherein the flexible hinge biases apart the clamshell halves of the support section.

12. The dispenser container assembly for storing and dispensing a dental implant device of claim 10, wherein the aperture formed by the features of the opposed contact edges of the clamshell halves is positioned opposite the flexible hinge.

13. The dispenser container assembly for storing and dispensing a dental implant device of claim 10, wherein the support section and the cap section are fabricated from a sterilizable polymeric resin material.

\* \* \* \* \*